US00PP34683P2

(12) United States Plant Patent
Iezzoni

(10) Patent No.: US PP34,683 P2
(45) Date of Patent: Oct. 25, 2022

(54) CHERRY TREE (ROOTSTOCK) NAMED 'LINCOLN'

(50) Latin Name: ***Prunus cerasus* L.**
Varietal Denomination: Lincoln

(71) Applicant: BOARD OF TRUSTEES OF MICHIGAN STATE UNIVERSITY, East Lansing, MI (US)

(72) Inventor: Amy Iezzoni, Cedar, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 17/300,890

(22) Filed: Dec. 8, 2021

(51) Int. Cl.
*A01H 5/06* (2018.01)
*A01H 6/74* (2018.01)

(52) U.S. Cl.
USPC ..... Plt./183

(58) Field of Classification Search
USPC ..... Plt./156, 180, 181, 183
See application file for complete search history.

(56) References Cited

U.S. PATENT DOCUMENTS

| | | | |
|---|---|---|---|
| PP8,954 | P | 10/1994 | Gruppe et al. |
| PP9,622 | P | 8/1996 | Gruppe et al. |
| PP16,173 | P3 | 12/2005 | Gruppe et al. |
| PP30,538 | P3 | 5/2019 | Iezzoni |
| PP30,553 | P3 | 6/2019 | Iezzoni |
| PP32,813 | P3 | 2/2021 | Iezzoni |
| PP32,852 | P3 | 3/2021 | Iezzoni |

OTHER PUBLICATIONS

"Bing Cherry: Prunus Avium Bing", Arbor Day Foundation, pp. 1-3, 2021.
"Montmorency Cherry: Prunus Cerasus Montmoren", Arbor Day Foundation, pp. 1-3, 2021.
"Sweet Cherry Hedelfingen: Prunus Avium", My Garden Life, pp. 1-3, 2021.
"The English Morello Cherry Tree", Minnetonka Apple Orchards, pp. 1-14, 2021.
"Sumadinka", Zomi Komerc D.O.O., Bela Voda, 1 page, 2022.

*Primary Examiner* — Karen M Redden
(74) *Attorney, Agent, or Firm* — McKee, Voorhees & Sease, PLC

(57) ABSTRACT

A new cherry tree variety suitable for use as rootstock.

3 Drawing Sheets

Botanical designation: The present invention relates to a new *Prunus cerasus* L. cherry tree variety.

Variety denomination: The new plant has the varietal denomination 'Lincoln.'

BACKGROUND OF THE INVENTION

This invention relates to a new and distinct variety cherry tree. In the field of plant genetics, researchers conduct an extensive and continuing plant-breeding program including the organization and asexual reproduction of orchard trees, and of which plums, peaches, nectarines, apricots, cherries, almonds and interspecifics are exemplary. It was against this background of activities that the present variety of cherry tree was originated and asexually reproduced in our experimental orchard.

PRIOR VARIETIES

Among the existing varieties of cherry trees, which are known to us, and mentioned herein 'Akastoi Korai' (not patented); 'English Morello' (not patented); 'Sumadinka' (not patented); 'Gisela 3' (Test Name 'GI 2091', U.S. Plant Pat. No. 16,173), 'Gisela 5' (Test Name 'GI 148/2', U.S. Plant Pat. No. 9,622), and 'Gisela 6' (Test Name 'GI 148/1', U.S. Plant Pat. No. 8,954), 'Clinton' (U.S. Plant Pat. No. 30,538) , 'Cass' (U.S. Plant Pat. No. 30,553), 'Lake' (U.S. Plant Pat. No. 32,813), 'Clare' (U.S. Plant Pat. No. 32,852), 'Crawford' (U.S. Plant Pat. No. 30,473), 'Hedelfingen' (not patented); 'Bing' (not patented); and 'Montmorency' (not patented)

ORIGIN OF THE VARIETY

'Lincoln' originated from a hand-pollinated cross performed in 1993 between the selection 'II 6(3)' and the cultivar 'Akastoi Korai' in Clarksville, Mich. The maternal parent 'II 6(3)' originated from a hand-pollinated cross performed in 1983 between the cultivars 'English Morello' and 'Sumadinka'. 'Lincoln' was originally designated by its field number, 26e7(18), and prior to advanced field testing it was named 'Lincoln'.

The seedling that gave rise to 'Lincoln' was planted in Clarksville, Mich. in 1996 and was propagated asexually by cuttings in 1999 to provide materials for the first rootstock evaluations. 'Lincoln' rootstock was selected as promising based on initial trials planted in Clarksville, Mich. in 2002 with 'Hedelfingen' scion and in Prosser, Wash., planted in 2002 with 'Bing' scion. Meristem culture-derived rootstocks of 'Lincoln' were subsequently produced, budded with 'Montmorency' scion, and the trees were planted in Traverse City, Mich. in 2011 for further evaluation.

ASEXUAL REPRODUCTION OF VARIETY

Asexual reproduction of the 'Lincoln' cherry rootstock was achieved using the mother plant to obtain rooted liners using conventional softwood cutting procedures, and through meristem culture with commercial nurseries. Initially, liners were propagated from softwood cuttings in commercial greenhouses. A subset of these liners was used to establish a mother block in Clarksville, Mich. The remaining liners were sent to a nursery to make test trees of 'Lincoln' that were budded with the scion 'Hedefingen' and 'Bing'. The resulting trees with 'Hedefingen' and 'Bing' scion were planted in trials in Clarksville, Mich. and Prosser, Wash., respectively. A second set of liners was propagated from meristem culture. These 'Lincoln' liners were budded with 'Montmorency' scion to make trees for a trial in Traverse City, Mich. The living tissues (i.e. leaves, stems, buds, flowers and fruits) of the original mother block plants were observed to be identical to secondary and tertiary vegetatively propagated plants.

STATEMENT OF STABILITY

Asexual propagation as described has demonstrated that the combination of traits that characterize this tree are fixed and remain true to type through at least two successive propagation cycles.

SUMMARY OF THE INVENTION

'Lincoln' is particularly useful as a rootstock. 'Lincoln' cherry rootstocks result in smaller trees than standard 'mahaleb' and 'mazzard' rootstocks, with trees sizes similar to 'Gisela® 6'. The rootstocks do not induce precocity as the other 'Clinton', 'Cass', 'Lake', 'Clare' and 'Crawford' rootstocks or 'Gisela®' rootstocks. 'Montmorency' trees on 'Lincoln' were observed to have high yields in mature orchards. Therefore, 'Lincoln' rootstocks offer increased planting density without the associated crop load management issues associated with highly dwarfing precocious rootstocks. 'Lincoln' is suitable for standard nursery propagation practices for uniform liner production.

COMPARISON WITH PARENTS

The seed parent of the new cherry variety, 'II 6(3)', is a hybrid from the cross between the cultivars 'English Morello' (a landrace variety from Germany) and 'Sumadinka' (a bred variety from Serbia). Its pollen parent, 'Akastoi Korai', is a Hungarian landrace cherry variety. All the progeny from the cross, including the individual that was selected and named 'Lincoln', were distinguishable from each of its parents as the parents were heterozygous and had different origins. Thus, the progeny population from which 'Lincoln' was selected exhibited the segregation expected with the use of divergent heterozygous parents. The parents are unavailable for morphological comparison.

COMPARISON WITH KNOWN RELATED CULTIVARS

The new cherry variety may be distinguished from known related cultivars, for example the 'King', by a combination of several characteristics. First, the number of lenticels is medium for 'Lincoln' and few for 'King'. The shape of the apex of vegetative bud is obtuse for 'Lincoln' and acute for 'King', the ratio of length to width of leaf blade is small for 'Lincoln' and medium for 'King', the flower pedicel length is 10 mm for 'Lincoln' and 20 mm for 'King', mature fruit shape is kidney for 'Lincoln' and flat spherical for 'King' among other traits.

TABLE 1

Comparative Data Table

| Characteristics | 'Lincoln' |
|---|---|
| Vigor - TCSA | Similar to 'Gi6' |
| Vigor - canopy | Similar to 'Gi6' |
| Precocity | Low (Less than 'Clinton', 'Cass', 'Lake', 'Clare' and 'Crawford' and 'Gisela ® 3, 5 & 6') |
| Fruit size | Similar to 'Gi6' |
| Graft compatibility[1] | Good (limited scions tested) |
| Needs support | No |
| Root suckers | + (few) |
| Mid-winter cold stress | Tolerant |

[1]Ratings are based on trees with 'Bing', 'Hedelfingen', and 'Montmorency' scions.

The 'Lincoln' cherry rootstocks result in smaller trees than standard 'mahaleb' and 'mazzard' rootstocks, with trees sizes similar to 'Gisela® 6'. These rootstocks do not induce precocity as the other 'Clinton', 'Cass', 'Lake', 'Clare' and 'Crawford' rootstocks or 'Gisela®' rootstocks. 'Montmorency' trees on 'Lincoln' were observed to have high yields in mature orchards. Therefore, 'Lincoln' rootstocks offer the potential for increased planting density without the associated crop load management issues associated with highly dwarfing precocious rootstocks.

BRIEF DESCRIPTION OF PHOTOGRAPHS

The accompanying photographs display flowers, leaves, and fruits from a self-rooted mother block tree at Clarksville, Mich. in April 2021.

DESCRIPTION OF THE NEW VARIETY

Figure 1:
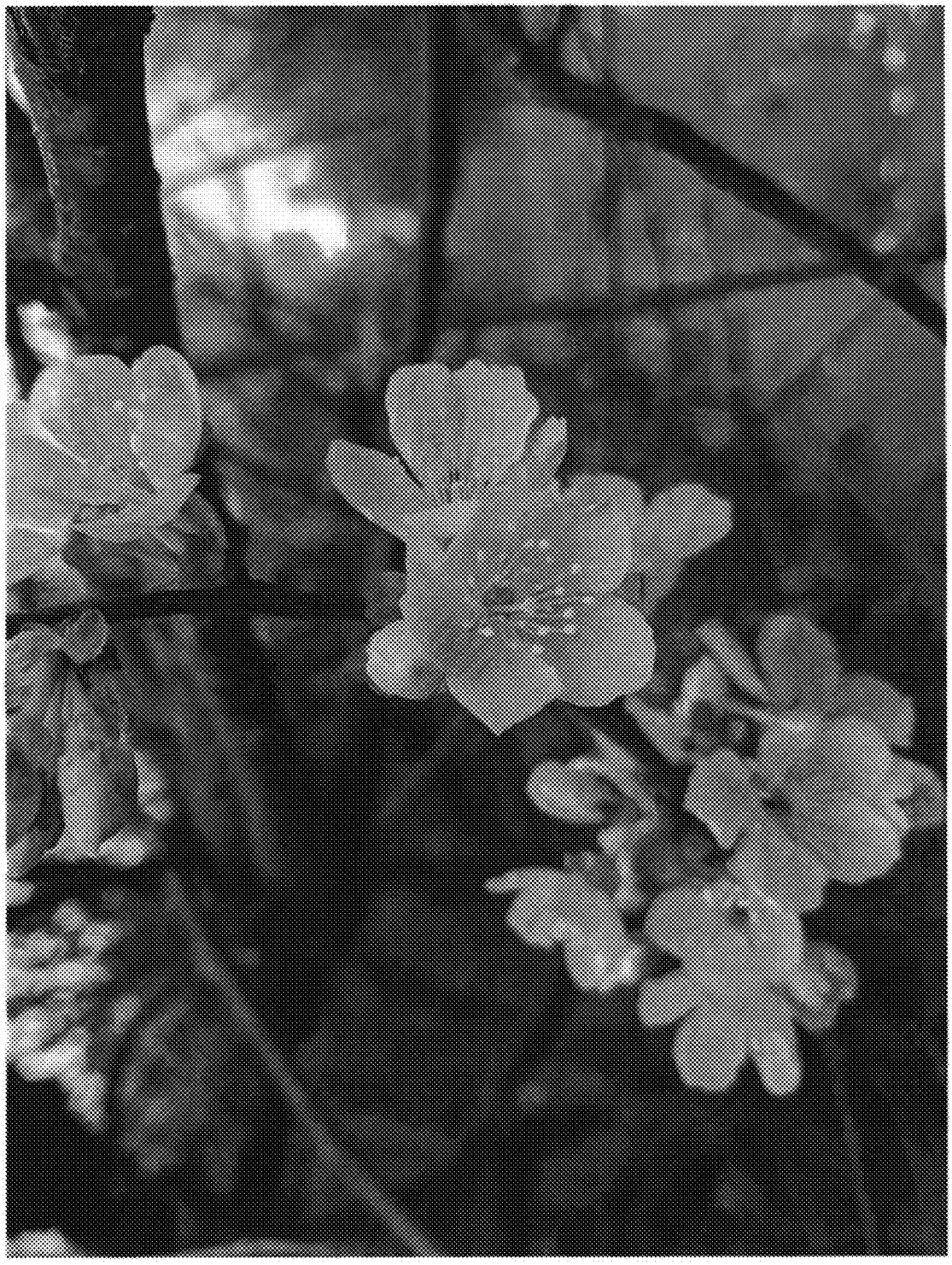
FIG. 1 is a photograph of the flowers of 'Lincoln'.
Figure 2:
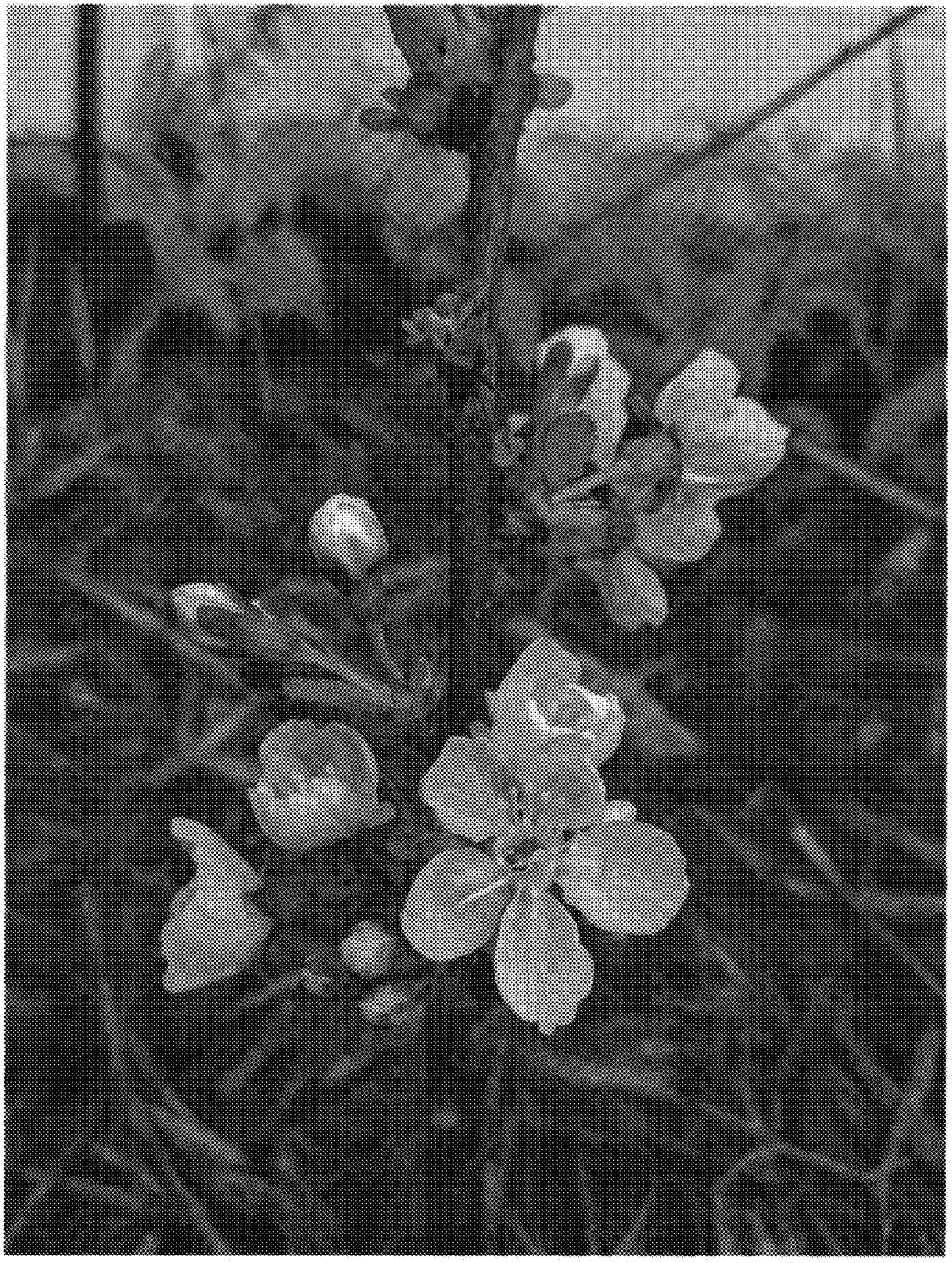
FIG. 2 is a photograph of a branch of 'Lincoln'.
Figure 3:
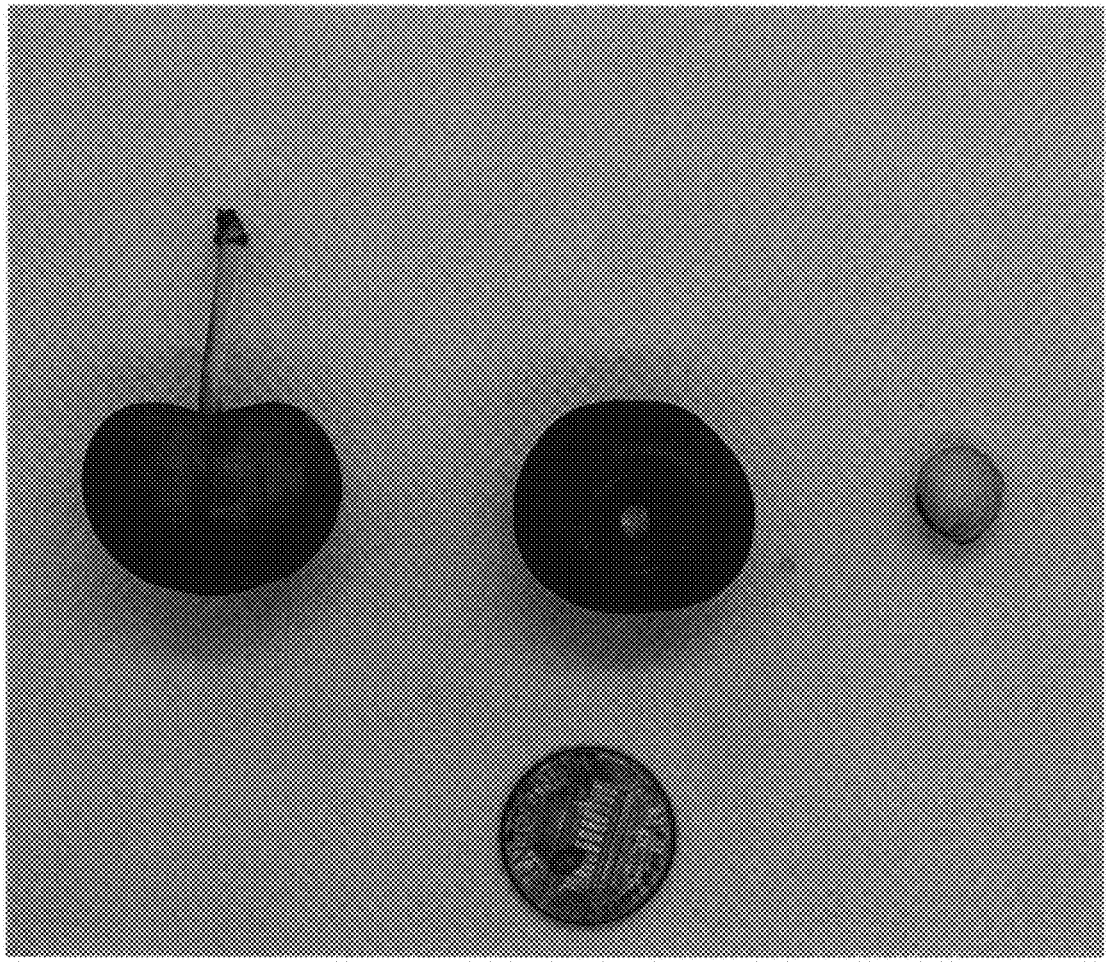
FIG. 3 is a photograph of fruit of 'Lincoln'.

The following is a detailed botanical description of the new variety of cherry tree, its flowers, foliage and fruit, as based on observations of various aged specimens grown in Clarksville, Mich. with color in accordance with The Royal Horticultural Society Colour Chart (RHS), 2001 edition.

Measurement details:

Flowers:

*Inflorescence height.*—Measured from where the flower cluster attaches to the branch to the most distal floral part.

*Flower diameter.*—Measured across the petals in mm.

*Flower length.*—Measured from the bottom of the pedicel to the most distal flower point (mm).

*Pedicel.*—The stem of an individual flower. It is measured from the attachment in the bud to the start of the perianth.

*Peduncle.*—A stalk supporting an inflorescence. In these selections, the cherry flowers within a flower bud all start at the same base and they the stalk separates into individual pedicels supporting each flower.

*Anther color.*—Before the anther's dehisce, when they are still bright yellow and plump.

*Anther length.*—Measured for the longest anther measured from the top of the perianth tube.

*Style.*—Measured above the swelled ovary.

Characteristics:

Tree:

*Plant height.*—Approx. 5.5 m.
*Plant vigor.*—Medium.
*Plant habit.*—Spreading.
*Plant branching.*—Strong.
*Hardiness.*—Cold resistant, drought/heat tolerance not exhibited.
*Scion compatibility confirmed.*—'Bing', 'Hedelfingen', 'Montmorency'.

One year old shoot:

*Thickness.*—5 mm.
*Length of internode.*—2.5 cm.
*Pubescence.*—Absent.
*Relative number of lenticels.*—Medium.
*Anthocyanin coloration of apex.*—Absent.
*Position of vegetative bud in relation to shoot.*—Markedly held out.
*Shape of apex of vegetative bud.*—Obtuse.

Leaves:

*Mature leaf arrangement.*—Alternate.
*Intensity of anthocyanin coloration of young leaf.*—Weak.
*Leaf blade shape.*—Ovate.
*Leaf blade ratio length to width.*—Small.
*Leaf length (blade only).*—11 cm.
*Leaf width.*—6.5 cm.
*Leaf blade angle of apex.*—Acute.
*Leaf blade shape of base.*—Obtuse.
*Leaf blade shape of apex.*—Acute.
*Leaf blade incisions of margin.*—Crenate.
*Leaf blade depth of incisions of margin.*—Medium.
*Leaf blade glossiness of upper side.*—Medium.
*Leaf blade pubescence of lower side.*—Weak.
*Upper surface color.*—R.H.S. 137B.
*Leaf upper surface texture/pubescence.*—Smooth.
*Leaf upper surface venation color.*—R.H.S. 137C.
*Leaf venation pattern.*—Pinnate.
*Lower surface color.*—R.H.S. 138B.
*Petiole-intensity of pubescence of upper side.*—Weak.
*Petiole-depth of groove.*—Shallow.
*Leaf petiole length.*—18 mm.
*Leaf petiole diameter.*—2 mm.
*Leaf petiole color.*—R.H.S. 138B and 59A.
*Leaf-presence of nectaries.*—Present.
*Leaf-predominant number of nectaries.*—Two.
*Leaf-position of nectaries.*—Base of leaf blade & petiole.
*Nectary shape.*—Reniform.
*Leaf stipule length.*—13 mm.
*Leaf stipule width.*—2 mm.
*Leaf stipule shape.*—Pointed.
*Leaf stipule margin.*—Serrated.

Flowers:

*Fragrance.*—None.
*Bloom date* (50%).—Apr. 27, 2021.
*Inflorescence diameter.*—5 cm.
*Flower diameter.*—31 mm.
*Petal arrangement.*—Flat whorl.
*Petal margin.*—Smooth.
*Petal texture.*—Smooth.
*Petal color when fully open (upper surface).*—R.H.S 155D.
*Petal color when fully open (lower surface).*—R.H.S 155D.
*Sepal shape.*—Triangle.
*Sepal apex.*—Pointed.
*Sepal margin.*—Serrated.
*Sepal texture.*—Slightly pubescent.
*Sepal color upper.*—R.H.S 138A.
*Sepal color lower.*—Both R.H.S 138B and 59A.
*Flower pedical length.*—10 mm.
*Flower pedicel diameter.*—1 mm.
*Flower pedicel texture.*—Smooth.
*Flower pedicel color.*—Both R.H.S 144B and 59A.
*Flower peduncle length.*—1 mm.
*Flower peduncle diameter.*—2 mm.
*Flower peduncle texture.*—Smooth.
*Flower peduncle color.*—R.H.S 138B.
*Pistils-number per flower.*—1.
*Style length.*—9 mm.
*Style color.*—R.H.S 138D.
*Stigma shape.*—Round/indented.
*Stigma color.*—R.H.S 138D.
*Stamen filament color.*—R.H.S 155D.
*Longest anther length.*—9 mm.
*Anther color.*—R.H.S 20A.
*Pollen color.*—R.H.S 17C.

Fruit:

*Mature fruit shape.*—Kidney shape.
*Mature fruit height.*—19 mm.
*Mature fruit width* 1.—20 mm.
*Mature fruit width* 2.—25 mm.
*Mature fruit ratio height/width.*—2.
*Mature fruit weight.*—6 g.
*Mature fruit taste.*—Sour.
*Mature fruit skin color.*—R.H.S. 59A.
*Mature fruit flesh color.*—R.H.S. 46A.
*Stone color.*—R.H.S. 164D.
*Stone shape.*—Spherical.
*Stone number.*—1.
*Stone height.*—9 mm.
*Stone width*1.—10 mm.
*Stone width*2.—7.5 mm.
*Stone ratio height/width.*—2.
*Stone weight.*—0.3 g.
*Fruit stem length.*—30 mm.

Market use: Rootstock.

I claim:

1. A new and distinct variety of cherry tree named 'Lincoln', substantially as described and illustrated herein.

* * * * *